United States Patent [19]

Grat

[11] 4,063,823
[45] Dec. 20, 1977

[54] WORKPIECE, AND CONTAINER AND CONTENTS, INSPECTING APPARATUS AND METHOD

[75] Inventor: Felix R. Grat, Lake Hiawatha, N.J.

[73] Assignee: Rame-Hart, Inc., Mountain Lakes, N.J.

[21] Appl. No.: 750,460

[22] Filed: Dec. 14, 1976

[51] Int. Cl.² .......................................... G01N 21/24
[52] U.S. Cl. .............................. 356/197; 250/223 B; 356/240
[58] Field of Search ............................... 356/197, 240; 250/223 B

[56] References Cited

U.S. PATENT DOCUMENTS

| Re. 28,984 | 9/1976 | Drinkuth et al. | 358/106 |
| 3,479,514 | 11/1969 | Kidwell | 250/123 B |
| 3,576,442 | 4/1971 | Nakamura | 356/197 |
| 3,777,169 | 12/1973 | Walter et al. | 356/240 |
| 3,830,969 | 8/1974 | Hofstein | 356/197 |
| 3,914,058 | 10/1975 | Knapp et al. | 356/197 |

*Primary Examiner*—John K. Corbin
*Assistant Examiner*—R. A. Rosenberger
*Attorney, Agent, or Firm*—Thomas N. Neiman

[57] ABSTRACT

The method comprises directing light, in the visible light spectrum, of from approximately 4900 to 5800 Angstrom units onto workpieces, or onto containers having translucent bodies in order to illuminate the workpieces, or both the containers and fluent material contents of the containers, the method having a particular utility in inspecting workpieces in assembly or quality control operations, and in inspecting vials, ampoules, and the like, to evaluate and/or detect structural fissures, disconnections, fractures, etc. in such workpieces, and growths (i.e., egg embryos), foreign matter, and the like, in the fluent material contents of the containers, as well as the condition of the containers themselves. The apparatus comprises means suitable for practicing the novel method, and includes a support for the workpiece or fluent-material-confining container, a television system for viewing and displaying the illuminated workpiece or container and contents, and a light source which provides radiation substantially in a range of from 4900 to 5800 Angstrom units, for effecting the desired illumination of the container and contents, or workpiece, at not more than approximately 0.05 footcandle.

17 Claims, 1 Drawing Figure

U.S. Patent   Dec. 20, 1977   4,063,823
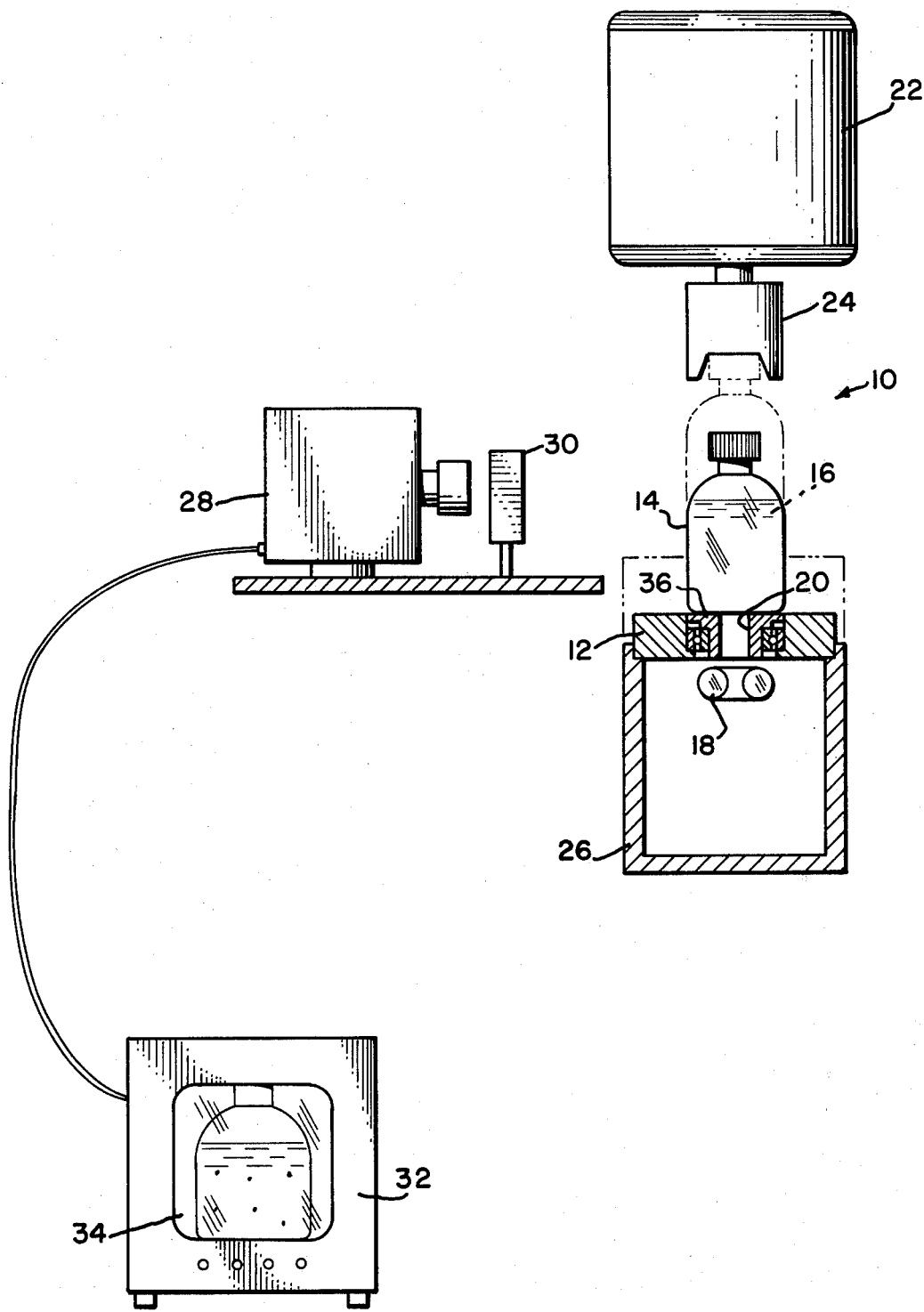

WORKPIECE, AND CONTAINER AND CONTENTS, INSPECTING APPARATUS AND METHOD

This invention pertains to inspection apparatus and methods, and in particular is concerned with the inspection of workpieces, or containers which have translucent bodies which are used for fluent materials, or in which fluent materials are confined, such as medicinals in vials, ampoules, and the like, veins and arteries, and similar venous structures, eggs, etc., in order that the condition of the workpieces, and the nature of the fluent materials and the containers themselves may be evaluated.

This is a crowded art, having a great deal of prior teaching, especially as pertains to the inspection of vials, ampoules and the like, and the contents thereof. U.S. Pat. No. 3,601,616, issued Aug. 24, 1971, to Takuma Katsumata et al., for a Method and Device for Inspecting Bottle by Radiant Energy, is typical. The teaching here, however, is for the inspection of empty containers, by inserting a light source into the bottle and reflecting back the internal illumination. Such is not suitable for containers which have fluent materials therein, especially where it is also or principally desirable to inspect the fluent materials themselves.

A very pertinent reference is comprised by U.S. Pat. No. 3,589,907, issued on Aug. 10, 1971, to William H. Drinkuth et al. (since reissued as Re. 28,984, on Sept. 28, 1976), for Article Inspection by Successively Televised Images. However, the teaching here is to discern foreign matter in the contents of a container by twice scanning the container and subjecting the two scannings to a comparison. Another reference, U.S. Pat. No. 3,627,423, issued to Julius Z. Knapp et al., on Dec. 14, 1971, for Method and Apparatus for Detecting Particular Matter in Sealed Liquids, comprises the formation of a "shadow zone" at the viewing axis. To this end, it is necessary to direct two light beams onto the container.

Other prior art of note includes U.S. Pat. No. 3,830,969, issued to Steven R. Hofstein, on Aug. 20, 1974, for a System for Detecting Particulate Matter; U.S. Pat. No. 3,479,514, comprising a Method and Means for Inspecting Glass Articles, issued to J. F. Kidwell, on Nov. 18, 1969; U.S. Pat. No. 3,029,349, issued to R. E. Schell, on Apr. 10, 1962, for an Inspection Apparatus; and U.S. Pat. No. 3,528,544, issued to Teiichi Neguchi et al., for a Method for Inspecting Liquids for Detection of Foreign Solid Matters, on Sept. 15, 1970.

It is apparent, from a review of the prior devices, that there exists a need for a simple and effective apparatus and method for inspecting workpieces and translucent containers and fluent materials contained within such containers. Accordingly, it is an object of this invention to set forth such a novel, simple and effective apparatus and method in which complicated, ancillary, interpretative or comparative equipment and/or circuitry, warranted by prior art apparatus and methods, is unnecessary.

Specifically, it is an object of this invention to disclose novel apparatus for inspecting translucent-body containers, and fluent materials contained within such containers, comprising means for disposing a translucent-body container, having fluent material therewithin, in an attitude for illumination thereof from an external source of light; a source of light; and means for directing light from said source onto a fluent-material-containing, translucent-body container disposed therefor by said container disposing means, to cause illumination of both said container and fluent material therewithin; wherein said light source produces illuminative radiation in which a substantial portion thereof is within a range of approximately from 4900 to 5800 Angstrom units.

It is another object of this invention to set forth an apparatus for inspecting a workpiece, comprising means for disposing a workpiece in an attitude for illumination thereof from an external light source; a source of light which produces illuminative radiation in which a substantial portion thereof is within a range of approximately from 4900 to 5800 Angstrom units; means for directing light from said source onto a disposed workpiece; and means for displaying a pictorial image of such workpiece illuminated by said source at a location spaced apart from said workpiece-disposing means; wherein said displaying means comprises a television camera and a television receiver, said camera being disposed for viewing a workpiece illuminated by said source, and said receiver being disposed at said location and operatively coupled to said camera to display a video image of such workpiece under illumination.

It is another object of this invention to teach a method of inspecting translucent-body containers, and fluent materials contained within such containers, comprising the steps of disposing a translucent-body container, having fluent material therewithin, in an attitude for illumination thereof from an external light source; providing a light source which is productive of illuminative radiation in which a substantial portion thereof is within a range of approximately from 4900 to 5800 Angstrom units; and directing light from said source onto a fluent-material-containing, translucent-body container disposed therefor to cause illumination of both said container and fluent material contained therewithin.

Too, it is an object of this invention to teach a method of inspecting a workpiece, comprising the steps of disposing a workpiece in an attitude for illumination thereof from an external light source; providing a light source which is productive of illuminative radiation in which a substantial portion thereof is within a range of approximately from 4900 to 5800 Angstrom units; directing light from said source onto said workpiece; and displaying a pictorial image of said workpiece illuminated by said light source; wherein said displaying step comprises viewing the workpiece illuminated by said light source with a television camera, operatively coupling a television receiver to said camera, and displaying said image by said receiver.

Further objects of this invention, as well as the novel features thereof, will become more apparent by reference to the following description taken in conjunction with the accompanying FIGURE, the latter being a pictorial presentation of an embodiment which the apparatus may take for inspecting translucent-body containers and fluent materials contained within such containers, which embodiment is capable of practicing the novel methods.

As shown in the FIGURE, an embodiment of the apparatus 10 comprises a platform 12 upon which to receive the subject of the inspection, i.e., a workpiece, or a translucent-body vial, ampoule, bottle, or the like, in which is sealed a fluent material. In the depiction, the object of inspection is a bottle 14, and the contained fluent material is denoted by the index number 16. The platform 12 is supported above a light source 18 which, via an aperture 20 formed in the platform 12, is exposed to the bottle 14.

With respect to my novel method for inspecting a translucent-body container in which fluent material is confined, it is a part of my method to cause a rotation of the container. Hence, means (not shown) support a rotational motor 22, the motor having an output chuck 24 disposed for engaging the top of the vial or bottle 14. Too, other means (also not shown) are employed for selectively elevating and lowering a housing 26, in which a light source 18 is carried, to bring the bottle 14 into engagement with the chuck -- in order that the latter will impart rotation to the bottle, and to cause the fluent material to swirl. Patently, if desired, the apparatus could be modified to effect a lowering and elevation of the chuck 24, rather than the platform 12; this is a matter of choice. Also, in the use of the apparatus 10 in the inspection ("candling") of eggs, it will not be necessary to cause rotation. Too, it will be preferred to address the illumination to the top of the eggs; in inspecting embryonic eggs, the inspector is looking for the location of the air sac (which should be at the top of the egg) and checking the viability of the egg by looking for a healthy blood vessel structuring. Both of these signal conditions are to be found at the top of an egg.

A television camera 28 is supported for viewing of the bottle 14 and fluent material 16, via a shutter (in accord with practices well known in the art, and deemed to require no detailing here) 30. A television receiver 32, operatively coupled to the camera 28, displays on the screen 34 thereof, a pictorial view of the bottle 14 and fluent contents 16. Finally, platform 12 comprises a turntable 36 received in a bearing 38, in order that the bottle 14 might revolve about its axis, upon being driven by the chuck 24.

If the light source 18 were a bright, intense, white light, there would be considerable amplification and scattering of light at both the bottom wall of the bottle 14 and also across the level of the fluent contents 16. Thus, it is a teaching of my invention, not unlike that set forth in U.S. Pat. No. 3,479,514 (priorly cited), to employ a light source which produces a low illumination level emission which will have a low surface reflectivity. It is my invention to employ a light source which presents an output substantially in the 4900 to 5800 Angstrom units' portion of the visible light spectrum. By way of example, such a light is available from Aristo Grid Lamp Products, Inc., of Port Washington, Long Island, N.Y. By using such a light source, then, there will be no *brilliance*-obscuring of the fluent contents which are adjacent the bottom of the bottle 14 and on or adjacent the uppermost level of the contents 16. Rather, quite uniformly, the bottle and contents 16 are illuminated and display their natures most clearly on the screen 34.

The teaching in U.S. Pat. No. 3,479,514 is of interest, respecting this use of a light having a low illumination level emission. However, I have found that neither a white light, nor a *blue* light (per U.S. Pat. No. 3,479,514), nor light sources of other apparent hues — save for one: dominant green — have any particular affinity for, or are complementary to, television systems. Now then, as a television system is especially suitable for use in conjunction with the illumination of translucent-body containers and contents, and the illumination of workpieces, it is my discovery that light which is substantially within the 4900 to 5800 Angstrom units range, and at an input level of only approximately 0.05 foot-candle, will minimize the surfac reflectivity and light scattering arising from the use of white light, affords an optimum system responsiveness, and gives excellent definition in a television viewing system. Hence, my teaching of the deployment of a light source 18 which has an emission substantially in the cited Angstrom units range and 0.05 foot-candle input level.

Further to enhance the singular definition and discrimination of the depicted apparatus 10, the television camera 28 comprise a unit which employs a Newvicon tube, as the latter is especially highly responsive to low levels of light energy in the 4900 to 5800 Angstrom units range. Such cameras are readily available (under the brand name: Panasonic, Catalog No. WV241M, for instance). Finally, to complement the enhanced sensitivity of the "viewing system", the television receiver 32 comprises a unit having a screen with a phospher colorimity of 9300°, F phosphor.

At this point, and as known from the teachings of the prior art apparatus, the use of my apparatus 10 will be self-evident. In the inspection of a subject such as bottle 14 having fluent contents therein, motor 22 via the chuck 24 is caused to spin the bottle 14 — whereby the contents 16 will be set into circulating motion. Then, by slowing the rate of spin of the bottle 14, still-moving particulate matter (if any) will be discerned on the screen 34 of the receiver 32; the particulate matter will be swirling at substantially the original spin rate of the bottle. Also, any priorly moving "images" now seen to be rotating at the slower rate of spin will be discerned as scratches, cracks, or the like, or adherent matter in or on the bottle 14. Thus, external or adherent particulate matter, and defects in the bottle itself, are distinguished from internal, fluent material-borne particulate matter, simply by rotating the bottle 14 at a slower rate of spin than that originally induced in the fluent material.

The uses for the apparatus 10 are beyond speculation or anticipation. Clearly, the apparatus 10 has a present and immediate utility in the inspection of pharmaceutical fluids and their containers for deleterious, foreign matter. The apparatus 10 will also serve to display vial and/or ampoule inscriptions and coding, on surface-borne labels, in order to ascertain that contents of "batches" have been correctly culled and grouped. The apparatus 10, as noted, will reveal flaws in the bottle, clearly displaying cracks, scratches, broken seals, etc. therein.

My apparatus 10, as discussed priorly, is most suitable for the candling of eggs — embryonic, or otherwise. Toward the inspection of eggs to be used in the production of vaccines, there is no need to rotate the egg. Simply, the use of the 4900 to 5800 Angstrom units range light source, at only 0.05 foot-candle power, will clearly and discriminately illuminate the translucent-shell object, and display the air sac location and any blood vessel structure therein. In such inspection of eggs, or toward any other similar inspection, it is only necessary to dispose one or more eggs to a lamp or a battery of lamps providing the prescribed light source, and display the image(s) on the priorly described television receiver, having transmitted the low level illuminated subjects via the noted television camera (or equivalent). Means for supplying the eggs (or vials, ampoules, bottles, etc., or other "workpieces") to the lamp or lamps, for making or otherwise signalling "rejects," and for moving the inspected subjects off to another location, are deemed to be within the state of the art. Hence, no discussion of such is necessary here.

As for "workpieces;" there are unnumbered objects which require clear, discriminated inspection which is not possible with the human eye, and which is offered by my apparatus 10. By the simple expedient of enlarging the video display — either through an enlarger interposed between the subject and the camera, or through the use of a television receiver which itself enlarges the subject, minute structures can be monitored: microcircuitry on substrates, subminiature mechanisms, etc. Too, the apparatus 10 is useful in the inspection and display of microbiological colonies on a medium, in order that the nature and count of such colonies may be assayed. As venous structures are translucent, the apparatus 10 is also of singular utility in viewing, enlarging, and displaying such, in pursuit of the examination, for instance, of varicose veins — to discern irregularities, swelling, etc.

It was noted earlier that, alternatively, the subject bottle 14 could be raised to the motor and chuck 22 and 24, or vice versa. Too, in the inspection of eggs, microcircuitry, and like subjects, the motor 22 may be dispensed with or silenced. The light source 18 is shown at the base of the object, the bottle 14. However, the light source may be directed onto the top of a translucent-top article (i.e., egg), or an open-topped article (i.e., microbiological colonies on a medium, microcircuitry). Too, if desirable, the light source may be addressed to the side of a subject — a bottle, ampoule, vial, etc.; also the latter need not necessarily be vertically oriented, although bottle 14 is depicted thus. All such variations of arrangements of the novel apparatus, and the inventive method which it employs, are deemed to proceed from my teaching. Thus, while I have described my invention in connection with a specific embodiment thereof, capable of practicing the new methods herein disclosed, it is to be clearly understood that this is done only by way of example and not as a limitation to the scope of my invention as set forth in the objects thereof and in the appended claims.

I claim:

1. An improved apparatus for inspecting translucent-body containers, and fluent materials contained within such containers, having means for disposing a translucent-body container having fluent material therewithin in an attitude for illumination thereof from an external light source, having a source of light, and further having means for directing light from said source onto a fluent-material-containing, translucent-body container disposed therefor by said container disposing means, to cause illumination of both said container and fluent material therewithin, wherein the improvement comprises:
said light source comprises means restricting illumination of a fluent-material-containing, translucent-body container to only approximately 0.05 foot-candle, to minimize undue surface reflection and light scattering, and further comprises means providing illuminative radiation in which a substantial portion thereof is within a range of approximately from 4900 to 5800 Angstrom units.

2. Apparatus, according to claim 1, wherein:
not less than 51 percent of said portion is within said range.

3. Apparatus, according to claim 1, wherein:
substantially all of said radiation is within said range.

4. Apparatus, according to claim 1, wherein:
said container-disposing means comprises means for effecting movement of a translucent-body, fluent-material-containing container.

5. Apparatus, according to claim 4, wherein:
said movement-effecting means includes means for moving a container in a plurality of directions.

6. Apparatus, according to claim 5, wherein:
said moving means comprises means for moving a container in both rotary and translating directions.

7. Apparatus, according to claim 1, further including:
means for displaying a pictorial image of a container and fluent material illuminated by said source at a location spaced apart from said container-disposing means.

8. Apparatus, according to claim 7, wherein:
said displaying means comprises a television camera and a television receiver, said camera being disposed for viewing a container and fluent material illuminated by said source, and said receiver being disposed at said location and operatively coupled to said camera to display a video image of such container and fluent material.

9. Apparatus, according to claim 8, wherein:
said camera comprises a video tube which is highly responsive to illumination in said range.

10. An improved apparatus for inspecting a workpiece, having means for disposing a workpiece in an attitude for illumination thereof from an external light source, having a source of light, and further having means for displaying a pictorial image of such workpiece illuminated by said source at a location spaced apart from said workpiece-disposing means, said displaying means comprising a television camera and a television receiver, said camera being disposed for viewing a workpiece illuminated by said source, and said receiver being disposed at said location and operatively coupled to said camera to display a video image of such workpiece under illumination, wherein the improvement comprises:
said light source comprises means restricting illumination of a workpiece to only approximately 0.05 foot-candle, to minimize undue surface reflection and light scattering, and further comprises means providing illuminative radiation in which a substantial portion thereof is within a range of approximately from 4900 to 5800 Angstrom units.

11. An improved method of inspecting translucent-body containers, and fluent materials contained within such containers, comprising the steps of disposing a translucent-body container, having fluent material therewithin, in an attitude for illumination thereof from an external light source, providing a light source, and directing light from said source onto a fluent-material-containing, translucent-body container disposed therefor to cause illumination of both said container and fluent material contained therewithin, wherein the improvement comprises:
said light source providing step comprises providing an illumination restricted to only approximately 0.05 foot-candle, to minimize undue surface reflection and light scattering, and further comprises providing a light source having an illuminative radiation in which a substantial portion thereof is within a range of approximately from 4900 to 5800 Angstrom units.

12. A method, according to claim 11, wherein:

said light source-providing step comprises providing a source in which not less than fify-one percent of said portion is within said range.

13. A method, according to claim 11, wherein:
said light source-providing step comprises providing a source in which substantially all of said radiation is within said range.

14. A method, according to claim 11, further including the step of:
displaying a pictorial image of a container and fluent material illuminated by said light-directing step at a location spaced apart from said source.

15. A method, according to claim 4, wherein:
said displaying step comprises viewing a container and fluent material illuminated by said light-directing step with a television camera, operatively coupling a television receiver to said camera, and displaying said image by said receiver.

16. A method, according to claim 15, wherein:
said viewing step comprises viewing a fluent-material-containing, translucent-body container with a television camera having a video tube which is highly responsive to said range.

17. An improved method of inspecting a workpiece, comprising the steps of disposing a workpiece in an attitude for illumination thereof from an external light source, providing a light source, directing light from said source onto said workpiece, and displaying a pictorial image of said workpiece illuminated by said light source, said displaying step comprising viewing the workpiece illuminated by said light source with a television camera, operatively coupling a television receiver to said camera, and displaying said image by said receiver, wherein the improvement comprises:
said light source providing step comprises providing an illumination restricted to only approximately 0.05 foot-candle, to minimize undue surface reflection and light scattering, and further comprises providing a light source having an illuminative radiation in which a substantial portion thereof is within a range of approximately from 4900 to 5800 Angstrom units.

* * * * *